United States Patent
Nagamura et al.

(10) Patent No.: US 11,540,507 B2
(45) Date of Patent: Jan. 3, 2023

(54) SOLUTION FOR CRYOPRESERVATION OF ANIMAL CELLS OR ANIMAL TISSUES, CRYOPRESERVED PRODUCT, AND CRYOPRESERVATION METHOD

(71) Applicant: The University of Tokyo, Tokyo (JP)

(72) Inventors: Tokiko Nagamura, Tokyo (JP); Yuka Mori, Tokyo (JP); Takahisa Shimadzu, Tokyo (JP)

(73) Assignee: The University of Tokyo, Toyko (JP)

( * ) Notice: Subject to any disclaimer, the term of this patent is extended or adjusted under 35 U.S.C. 154(b) by 778 days.

(21) Appl. No.: 16/344,798

(22) PCT Filed: Nov. 2, 2017

(86) PCT No.: PCT/JP2017/039668
§ 371 (c)(1),
(2) Date: Dec. 10, 2019

(87) PCT Pub. No.: WO2018/084228
PCT Pub. Date: May 11, 2018

(65) Prior Publication Data
US 2021/0169069 A1    Jun. 10, 2021

(30) Foreign Application Priority Data

Nov. 4, 2016 (JP) .............................. JP2016-216346

(51) Int. Cl.
*A01N 1/02* (2006.01)
*C12N 1/04* (2006.01)

(52) U.S. Cl.
CPC ............. *A01N 1/0221* (2013.01); *C12N 1/04* (2013.01)

(58) Field of Classification Search
CPC ................................ A01N 1/0221; C12N 1/04
See application file for complete search history.

(56) References Cited

U.S. PATENT DOCUMENTS 6,638,709 B2 * 10/2003 Tai ...................... A61L 27/3891
   623/23.72
2003/0035843 A1 * 2/2003 Livesey ................. A61K 39/12
   424/549
2006/0188984 A1 * 8/2006 Rudd ................... A61K 38/193
   435/372
2011/0274663 A1   11/2011 Shirono et al.
2012/0128641 A1 * 5/2012 Austen, Jr. ........... A01N 1/0221
   435/325
2013/0059286 A1   3/2013 Chang

FOREIGN PATENT DOCUMENTS

| EP | 3037523 A1 | 6/2016 |
| JP | 06-046840 A | 2/1994 |
| JP | 07-023780 A | 1/1995 |
| JP | 2015-142559 A | 8/2015 |
| JP | 2016-034279 A | 3/2016 |
| WO | 2009/057537 A1 | 5/2009 |
| WO | 2015/062267 A1 | 5/2015 |
| WO | 2015/066551 A2 | 5/2015 |
| WO | 2016/076428 A1 | 5/2016 |

OTHER PUBLICATIONS

International Search Report for International Patent Application No. PCT/JP2017/039668, dated Jan. 9, 2018, with English translation.
S. Wada et al., "Cord Blood Processing-Separation and Concentration: HES Method," Low Temp. Med., vol. 25, No. 1, pp. 54-58, 1999.
Gecai Chen et al., "Comparison of the Effects of Different Cryoprotectants on Stem Cells from Umbilical Cord Blood," Stem Cells International, vol. 2016, Dec. 7, 2015 (Dec. 7, 2015), pp. 1-7, XP055665649, US ISSN: 1687-966X, DOI: 10.1155/2016/1396783.
Y. Naaldijk, "Cryopreservation of Human Umbilical Cord-Derived Mesenchymal Stem Cells in Complex Sugar Based Cryoprotective Solutions," Journal of Biotechnology Letters, vol. 4, No. 2, Dec. 1, 2013 (Dec. 1, 2013), pp. 95-99, XP055680609.
Extended European Search Report for European Patent Application 17867675.5, dated April 7. 2020 (Apr. 7, 2020)/.

* cited by examiner

*Primary Examiner* — Blaine Lankford
(74) *Attorney, Agent, or Firm* — Honigman LLP

(57) ABSTRACT

The present invention provides a solution for cryopreservation of animal cells or animal tissues which substantially includes a cryoprotectant that contains 0.5 w/v % to 6.0 w/v % of dextran or derivatives thereof or salts thereof and contains dimethyl sulfoxide, and includes a physiological aqueous solution; a cryopreserved product of animal cells or animal tissues which includes animal cells or animal tissues, and includes the above-described solution for cryopreservation of animal cells or animal tissues; and a cryopreservation method of animal cells or animal tissues, which is a method using the above-described solution for cryopreservation of animal cells or animal tissues.

7 Claims, 5 Drawing Sheets

SOLUTION FOR CRYOPRESERVATION OF ANIMAL CELLS OR ANIMAL TISSUES, CRYOPRESERVED PRODUCT, AND CRYOPRESERVATION METHOD

TECHNICAL FIELD

The present invention relates to a solution for cryopreservation of animal cells or animal tissues, a cryopreserved product, and a cryopreservation method.

CROSS-REFERENCE TO RELATED APPLICATIONS

This application is a 35 USC § 371 United States national stage application of International Application No. PCT/JP2017/039668, filed Nov. 2, 2017, which claims priority to Japanese Application No. 2016-216346, filed Nov. 4, 2016, the contents of which are incorporated herein by reference.

BACKGROUND ART

Generally, in cryopreservation of cells, storage is performed using a cryoprotectant that contains a serum derived from humans or non-human animals or a protein component derived from serum, and dimethyl sulfoxide (DMSO) in many cases. However, in products used for regenerative medicine in clinic, it is desirable not to include serum derived from humans or non-human animals or a protein component derived from serum.

Patent Document 1 discloses a solution for cryopreservation which contains sodium carboxymethylcellulose, DMSO, and glucose, and does not contain natural components derived from animals.

In addition. Patent Document 2 discloses a method for preserving mammalian cells by using a physiological aqueous solution for cell transplantation which contains trehalose and dextran.

PRIOR ART DOCUMENTS

Patent Documents

Patent Document 1: Japanese Unexamined Patent Application, First Publication No. 2015-142559
Patent Document 2: Japanese Unexamined Patent Application, First Publication No. 2016-034279

DISCLOSURE OF THE INVENTION

Problems to be Solved by the Invention

The solution for cryopreservation disclosed in Patent Document 1 does not contain natural components derived from animals but contains sodium carboxymethylcellulose, and therefore it is difficult to use the solution for clinical purposes in regenerative medicine and the like.

In addition, the physiological aqueous solution for cell transplantation disclosed in Patent Document 2 does not contain natural components derived from animals and additives such as sodium carboxymethylcellulose, but a storage temperature is 0 to 37° C., and therefore quality and safety at the time of freezing cells are not secured.

The present invention has been made in view of the above circumstances, and provides a solution for cryopreservation of animal cells or animal tissues which enables freezing of cells while maintaining cell viability and which does not include natural components derived from animals, a cryopreserved product, and a cryopreservation method.

Means for Solving the Problems

As a result of extensive research to achieve the above object, the inventors of the present invention have found that it is possible to freeze cells while maintaining cell viability by using a solution for cryopreservation which includes a cryoprotectant that contains a specific concentration of dextran and DMSO, and therefore have completed the present invention.

That is, the present invention includes the following aspects.

A solution for cryopreservation of animal cells or animal tissues according to a first aspect of the present invention substantially includes a cryoprotectant that contains 0.5 w/v % to 6.0 w/v % of dextran or derivatives thereof or salts thereof, and dimethyl sulfoxide; and a physiological aqueous solution.

In the solution for cryopreservation of animal cells or animal tissues according to the first aspect, foe amount of dimethyl sulfoxide may be 1.0 v/v % to 15.0 v/v %.

Use solution for cryopreservation of animal cells or animal tissues according to the first aspect may further include citric acid or hydrates thereof or salts thereof, in which a pH of the solution may be 6.0 to 8.0.

The solution for cryopreservation of animal cells or animal tissues according to the first aspect may further include glucose.

In foe solution for cryopreservation of animal cells or animal tissues according to the first aspect, foe physiological aqueous solution may be a Ringer's bicarbonate solution.

A cryopreserved product of animal cells or animal tissues according to a second aspect of the present invention includes animal cells or animal tissues; and the solution for cryopreservation of animal cells or animal tissues according to the first aspect.

In the cryopreserved product of animal cells or animal tissues according to the second aspect, the animal cells or animal tissues may be derived from an umbilical cord or umbilical cord blood.

A cryopreservation method of animal cells or animal tissues according to a third aspect of the present invention is a method that uses the solution for cryopreservation of animal cells or animal tissues according to the first aspect.

(1) A solution for cryopreservation of animal cells or animal tissues characterized by including a cryoprotectant that contains 0.5 w/v % to 6.0 w/v % of dextran or derivatives thereof or salts thereof, and 1.0 v/v % to 15.0 v/v % of dimethyl sulfoxide; including a physiological aqueous solution; and not including natural components derived from animals.

(2) The solution for cryopreservation of animal cells or animal tissues described in (1), further including citric acid or hydrates thereof or salts thereof, in which a pH of the solution is 6.0 to 8.0.

(3) The solution for cryopreservation of animal cells or animal tissues described in (1) or (2) further including glucose.

(4) The solution for cryopreservation of animal cells or animal tissues described in any one of (1) to (3), in which the physiological aqueous solution is a Ringer's bicarbonate solution.

(5) Tire solution for cryopreservation of animal cells of animal tissues described in any one of (1) to (4), in which the natural component derived from animals is serum.

(6) A cryopreserved product of animal cells or animal tissues which is characterized by including animal cells or animal tissues; and the solution for cryopreservation of animal cells or animal tissues described in any one of (1) to (5).

(7) The cryopreserved product of animal cells or animal tissues described in (6), in which the animal cells or animal tissues are derived from an umbilical cord or umbilical cord blood.

(8) A cryopreservation method of animal cells or animal tissues which is characterized by using the solution for cryopreservation of animal cells or animal tissues described in any one of (1) to (5).

Effects of the Invention

According to the above aspects, it is possible to provide a solution for cryopreservation of animal cells or animal tissues which enables freezing of cells while maintaining cell viability and which does not include natural components derived from animals, a cryopreserved product, and a cryopreservation method.

BEST MODE FOR CARRYING OUT THE INVENTION

Figure 1:
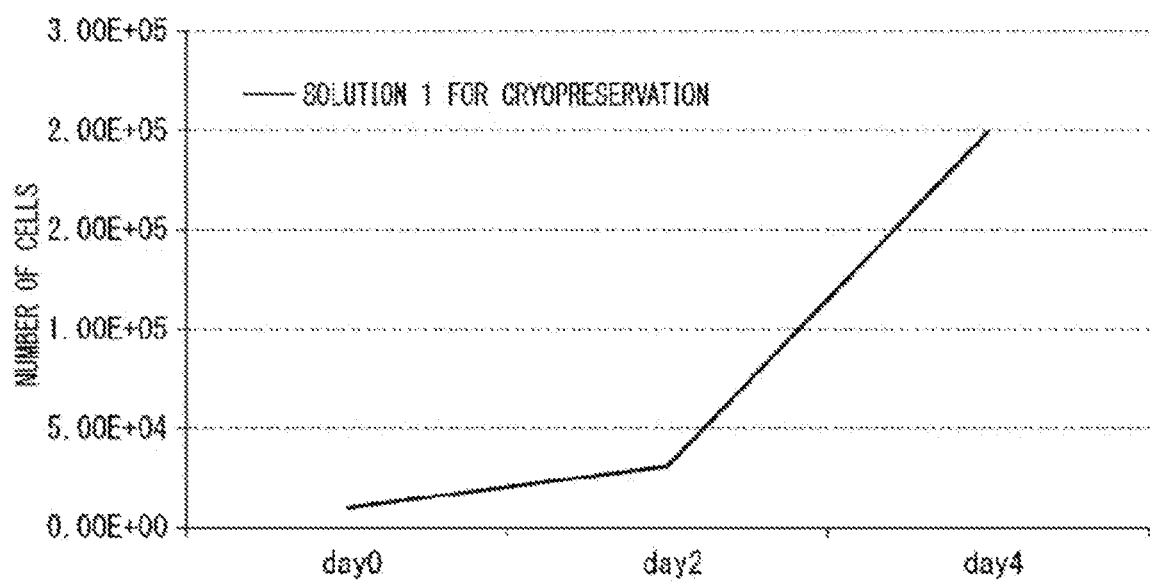
FIG. 1 is a graph showing the numbers of cells after 0, 2, and 4 days from culture performed after thawing umbilical cord-derived cells, which had been frozen by using a solution 1 for cryopreservation in Example 0.1.

<Solution for Cryopreservation of Animal Cells or Animal Tissues>

One embodiment provides a solution for cryopreservation of animal cells or animal tissues which substantially includes a cryoprotectant that contains 0.5 w/v % to 6.0 w/v % of dextran or derivatives thereof or salts thereof, and dimethyl sulfoxide; and a physiological aqueous solution.

According to the solution for cryopreservation of animal cells or animal tissues of the present embodiment, cells can be frozen while maintaining cell viability. In addition, animal cells or animal tissues, particularly human cells or human tissues, which are stored by using the solution for cryopreservation of the present embodiment, are not made to contain natural protein components derived from animals, and thickeners such as sodium carboxymethylcellulose or polyethylene glycol. Therefore, the solution for cryopreservation is very useful in clinical use.

In the present specification, the phrase "substantially including" means that the solution for cryopreservation includes only the above-mentioned components or includes other components to the extent that the effect of the above-mentioned components is not impaired. Furthermore, the solution for cryopreservation of the present embodiment particularly does not contain natural protein components derived from animals and thickeners as other components. Accordingly, as described above, the solution for cryopreservation is very useful in clinical use.

Examples of "natural components derived from animals" includes serum, a basal medium for animal cell culture, and the like. Examples of serums include adult cow serum, calf serum, newborn calf serum, fetal calf serum, and the like. Examples of basal media for animal cell culture include DMEM, EMEM, RPM1-1640, α-MEM, F-12, F-10, M-199, and the like.

Since the solution for cryopreservation of the present embodiment does not contain the above-mentioned natural components derived from animals (in particular, the solution is serum-free), the solution for cryopreservation does not cause the problem of differences in quality between lots of natural components derived from animals. In addition, it is possible to avoid the risk of change in cell properties due to components that are inherently unnecessary for cell storage, such as various cytokines, growth factors, and hormones contained in serum. Furthermore, it is possible to avoid effects due to components whose origin is unknown and which are contained in a basal medium for animal cell culture. Accordingly, a solution for cryopreservation which does not contain natural components derived from animals is very useful particularly in clinical use.

Furthermore, examples of animals front which cells or tissues, which are application targets for the solution for cryopreservation of the present embodiment, are derived, types of animal cells; and types of animal tissues are as described in the section of "<Cryopreserved products of animal cells or animal tissues" to be described later.

[Cryoprotectant]

The solution for cryopreservation of the present embodiment contains dextran and dimethyl sulfoxide (hereinafter referred to as "DMSO") as a cryoprotectant.

In general, a "cryoprotectant" means a substance used for the purpose of preventing various disorders due to freezing in order to maintain the functions anti viability of cells as much as possible. Examples of cryoprotectants used in the related art include DMSO, glycerin, trehalose, and the like.

In the solution for cryopreservation of the present embodiment, DMSO acts as an intracellular cryoprotectant by penetrating into cells, inhibiting formation of ice crystals, and thereby reducing damage to cells at the time of freezing.

In addition, in the solution for cryopreservation of the present embodiment, dextran acts as an extracellular cryoprotectant by being adsorbed onto a cell surface, inhibiting formation of ice crystals due to water and the like that has flowed out of the cell due to an osmotic pressure difference, and thereby inhibiting aggregation of cells.

(Dextran)

Dextran used for the solution for cryopreservation of the present embodiment is a polysaccharide $(C_6H_{10}O_5)_n$, consisting of D-glucose and has an α1→6 bond as its main chain. It is sufficient to use dextran having a molecular weight that enables dextran not to penetrate into cells.

Examples of weight-average molecular weights (Mw) of dextran include dextran 40 (Mw=40000), dextran 70 (Mw=70000), and the like, but examples are not limited thereto.

These dextrans may be produced by any known method such as chemical synthesis, production by microorganisms, or production by enzymes. In addition, commercially available products may be used. Examples of commercially available products of dextran include commercially available products such as Dextran 40 (manufactured by Otsuka Pharmaceutical Factory Inc.) and Dextran 70 (manufactured by Tokyo Chemical Industry Co., Ltd.).

Examples of dextran derivatives include dextran sulfuric acid, carboxylated dextran, diethylaminoethyl (DEAE)-dextran, and the like.

Examples of salts of dextran and derivatives thereof include acid addition salts of inorganic acids, acid addition salts of organic acids, metal salts, and basic salts, but examples are not limited thereto.

Examples of acid addition salts of inorganic acids include hydrochlorides, hydrobromates, hydroiodides, phosphates, nitrates, sulfates, acetates, and the like.

Examples of acid addition salts of organic acids include salts of propionic acid, sails of toluenesulfonic acid, salts of succinic acid, salts of oxalic acid, salts of lactic acid, salts of tartaric acid, salts of glycolic acid, salts of methanesulfonic acid, salts of butyric acid, salts of valeric acid, salts of citric acid, salts of fumaric acid, salts of maleic acid, salts of malic acid, and tire like.

Examples of metal salts include sodium salts, potassium salts, calcium salts, and the like.

Examples of basic salts includes ammonium salts, alkylammonium salts, and the like.

These salts are used as a solution at the time of use, and the action thereof is preferably the same as that of dextran. These salts may form hydrates or solvates. Any of these salts may be used alone or in combination of two or more thereof.

A content of dextran or derivatives thereof or salts thereof in the solution for cryopreservation of the present embodiment is preferably 0.5 w/v % to 6.0 w/v %, is more preferably 1.0 w/v % to 5.0 w/v %, mid is even more preferably 3.0 w/v % to 4.5 w/v %.

When the amount of dextran or derivatives thereof or salts thereof is equal to or more than the lower limit value described above, functions of dextran or derivatives thereof or salts thereof as an extracellular cryoprotectant can be more effectively performed. Meanwhile, when the amount of dextran or derivatives thereof or salts thereof is equal to or less than the upper limit value described above, aggregation of cells can be inhibited more effectively.

(Dimethyl Sulfoxide)

Regarding dimethyl sulfoxide (DMSO) used in the solution for cryopreservation of the present embodiment, it is preferable to use dimethyl sulfoxide with as high a purity as possible from the viewpoint of an influence on cells.

A content of DMSO in the solution for cryopreservation of the present embodiment is preferably 1.0 v/v % to 15.0 v/v %, is more preferably 5.0 v/v % to 12.5 v/v %, and is even more preferably 7.5 v/v % to 10.0 v/v %.

When the amount of DMSO is equal to or more than the lower limit value described above, DMSO penetrates into cells more effectively and inhibits formation of ice crystals. Therefore, damage to cells at the time of freezing can be reduced. Meanwhile, when the amount of DMSO is equal to or less than the upper limit value described above, cell cytotoxicity can be inhibited more effectively.

[Physiological Aqueous Solution]

As a physiological aqueous solution used in the solution for cryopreservation of the present embodiment, it is sufficient to use an isotonic aqueous solution in which a salt concentration, a sugar concentration, and the like are adjusted with sodium, potassium, and the like such that an osmotic pressure becomes almost the same as that of a body fluid or cell fluid. Examples of the physiological aqueous solution include a physiological salt solution, a physiological salt solution having a buffering effect (phosphate buffered saline (PBS), tris buffered saline (TBS), HEPES buffered saline, and the like), a Ringer's solution, a Ringer's lactate solution, a Ringer's acetate solution, a Ringer's bicarbonate solution, a 5% glucose aqueous solution, an isotonic agent (glucose, D-sorbitol, D-mannitol, lactose, sodium chloride, and the like), and the like, but examples are not limited thereto. Among them, a Ringer's bicarbonate solution is preferred.

Generally, a "Ringer's bicarbonate solution" is an isotonic aqueous solution containing magnesium, potassium, calcium, sodium, bicarbonate ions, and the like, and is used for the purpose of washing and storage of platelets. Respective concentrations of magnesium, potassium, calcium, sodium, and bicarbonate ions are not particularly limited as long as they are concentrations at which an osmotic pressure of tire Ringer's bicarbonate solution becomes close to that of a body fluid or cell fluid.

As the physiological aqueous solution, commercially available products may be used, or a prepared physiological aqueous solution may be used. Examples of commercially available products include OTSUKA NORMAL SALINE (manufactured by Otsuka Pharmaceutical Factory, Inc.) (physiological saline), Ringer's Solution "OTSUKA" (manufactured by Otsuka Pharmaceutical Factory, Inc.) (a Ringer's solution), Lactee (registered trademark) injection (manufactured by Otsuka Pharmaceutical Factory, Inc.) (a Ringer's lactate solution), VEEN-F INJECTION (manufactured by Kowa Pharmaceutical Co., Ltd.) (a Ringer's acetate solution), Otsuka Glucose Injection 5% (manufactured by Otsuka Pharmaceutical Factory, Inc.) (a 5% glucose solution), BICANATE (registered trademark) injection (manufactured by Otsuka Pharmaceutical Factory, Inc.) (a Ringer's bicarbonate solution), BICARBON (registered trademark) injection (manufactured by AY PHARMACEUTICALS CO., LTD.), and the like, but examples are not limited thereto.

In the present specification, the term "isotonic" means that an osmotic pressure is 250 mOsm/L to 380 mOsm/L.

A content of the physiological aqueous solution in the solution for cryopreservation of the present embodiment is 30 v/v % to 98.5 v/v % for example, is 30 v/v % to 95 v/v % for example, or is 40 v/v % to 90 v/v % for example.

[Other Components]

(pH Adjusting Agent)

A pH of the solution for cryopreservation of the present embodiment may be a value close to that in a living body. Specifically, a pH is preferably 6.0 to 8.0.

When a pH is within the above-described range, administration to a living body (for example, intravenously and the like) can be safety performed after thawing.

The solution for cryopreservation of the present embodiment preferably further includes a pH adjusting agent in order to adjust to the above-mentioned pH.

As a pH adjusting agent, an acid and salts thereof are preferred, but the pH adjusting agent is not particularly limited as long as a pH can be adjusted. Examples of acids include citric acid, lactic acid, phosphoric acid, acetic acid, gluconic acid, succinic acid, carbonic acid, hydrochloric acid, sulfuric acid, nitric acid oxalic acid, boric acid, or hydrates thereof, and the like.

In addition, as a salt of these acids, any salt may be used as long as it maintains a pH within the above range and does not have an action of oxidizing reduced biological molecules. A salt derived from the same type of acid as the above-described acids is preferred.

Examples of the salts of the acids include citrates, lactates, phosphates, acetates, gluconates, succinates, carbonates, bicarbonates, hydrochlorides, sulfates, nitrates, oxalates, borates, and a salt of two or more of these acids, and the like, but examples are not limited thereto.

Examples of citrates include sodium citrate, disodium, citrate, trisodium citrate, and hydrates of these, and the like.

Examples of lactates include sodium lactate, potassium lactate, calcium lactate, and the like.

Examples of phosphates include disodium hydrogenphosphate, potassium dihydrogenphosphate, and the like.

Examples of acetates include sodium acetate and the like.

Examples of gluconates include sodium gluconate and the like,

Examples of succinates include sodium succinate, disodium succinate, and hydrates thereof, and the like.

Examples of carbonates include ammonium carbonate, potassium carbonate, calcium carbonate, sodium carbonate, magnesium carbonate, and the like.

Examples of bicarbonates include ammonium hydrogencarbonate, potassium hydrogencarbonate, calcium hydrogencarbonate, sodium hydrogencarbonate (sodium bicarbonate), and the like.

Examples of hydrochlorides include ammonium chloride, sodium chloride, potassium chloride, and the like.

Examples of sulfates include ammonium sulfate, sodium sulfate, magnesium sulfate, and the like.

Examples of nitrates include ammonium nitrate, potassium nitrate, sodium nitrate, sodium nitrite, and the like.

Examples of oxalates include ammonium oxalate, sodium oxa late, and the like.

Examples of borates include sodium metaborate, sodium tetraborate, and the like.

Examples of salts of two or more acids described above include calcium lactate gluconate and the like.

Among these, as the pH adjusting agent, citric acid or hydrates thereof or salts thereof is preferable, and a citric acid hydrate or a sodium citrate hydrate is more preferable from the viewpoint that they are a compound present in a living body.

As the pH adjusting agent, commercially available products may be used, or a prepared pH adjusting agent may be used. Examples of commercially available products include the solution A in the biological products standard blood preservation solutions (hereinafter referred to as an "ACD-A solution") and the like, but examples are not limited thereto.

A content of the pH adjusting agent in the solution for cryopreservation of the present embodiment is preferably 0.01 w/v % to 1.0 w/v %, and is more preferably 0.05 w/v % to 0.5 w/v %.

When the amount of the pH adjusting agent is within the above-described range, a pH of the solution for cryopreservation can be maintained within the range close to that of a living body.

(Saccharides)

The solution for cryopreservation of the present embodiment may further contain saccharides. The saccharides are not particularly limited, and examples thereof include polysaccharides, oligosaccharides, disaccharides, monosaccharides, and the like.

Examples of polysaccharides include starch, glycogen, and foe like.

Examples of oligosaccharides include raffinose, stachyose, and the like.

Examples of disaccharides include sucrose, maltose, and the like.

Examples of monosaccharides include hexose, pentose, and the like.

Examples of hexoses include aldohexose, ketohexose, deoxy sugars, and the like.

Examples of aldohexoses include allose, altrose, glucose, mannose, gulose, idose, galactose, talose, and foe like.

Examples of ketohexoses include psicose, fructose, sorbose, tagatose, and the like.

Examples of deoxy sugars include fucose, fuculose, rhamnose, and the like.

Examples of pentoses include ribulose, xylulose, ribose, arabinose, xylose, lyxose, and the like.

Among them, a saccharide is preferably glucose because it becomes an energy source necessary for growth of animal cells or animal tissues after thawing.

A content of saccharides in tire solution for cryopreservation of the present embodiment is preferably 0.5 v/v % to 10.0 w/v %, and is more preferably 1.05 w/v % to 10.0 w/v %, is even more preferably 2.05 w/v % to 8.0 w/v %, and is particularly preferably 2.05 w/v % to 5.0 w/v %.

When the amount of saccharides is within the above-described range, it is possible to sufficiently supply an energy source necessary for growth of animal cells or animal tissue after thawing.

<Cryopreserved Products of Animal Cells or Animal Tissues>

In one embodiment, the present invention provides a cryopreserved product of animal cells or animal tissues which includes animal cells or animal tissues and the above-described solution for cryopreservation of animal cells or animal tissues.

According to the cryopreserved product of animal cells at animal tissues of the present embodiment, since the solution for cryopreservation which does not contain natural components derived from animals is used, animal cells or animal tissues can be used for clinical purposes as they are after being thawed.

In the present embodiment, an animal from which cells or tissues are derived is preferably a mammal.

Examples of mammals include rodents, lagomorphs, ungulates, carnivores, primates, and the like, and examples are not limited thereto.

Examples of rodents include mice, rats, hamsters, guinea pigs, and the like.

Examples of lagomorphs include rabbits and the like.

Example ungulates include pigs, cattle, goats, horses, sheep and the like,

Examples of carnivores include dogs, cats, and the like.

Examples of primates include humans, monkeys, rhesus macaques, crab-eating macaques, marmosets, orangutans, chimpanzees, and the like.

Among them, the animals are preferably mice and humans from the viewpoint that they are used in experimental or clinical applications.

In addition, in the present embodiment, examples of animal cells include stem cells administered via blood vessels for regenerative medicine and the like, pancreatic islet cells which are intravenously administered to patients with type 1 diabetes, dendritic cells which are intravenously administered to cancer patients, monocytes, natural killer (NK) cells, T cells (such as alpha beta (αβ) T cells, gamma delta (γδ) T cells, cytotoxic T cells (cytotoxic T lymphocyte; CTL), and helper T cells), B cells, macrophages, neutrophils, eosinophils, mesenchymal cells, and the like.

Among the above-mentioned cells, NK cells, T cells, and B cells are collectively referred to as "lymphocytes" in some cases, and monocytes and lymphocytes are collectively referred to as "mononuclear cells" in some cases.

These cells can be isolated by a known general method. For example, leukocytes, T cells, helper T cells, cytotoxic T cells, and γδ T cells can be isolated from, for example, a hemolyzed sample of peripheral blood or umbilical cord blood by fluorescence activated cell sorting (FACS) which uses an antibody against a cell surface marker. Alternatively, for example, isolation can be performed from a hemolyzed sample of peripheral blood or umbilical cord blood by an automated magnetic cell separator (autoMACS) which uses an antibody against a cell surface marker labeled with a cell labeling substance, and an antibody conjugated to an antibody against such a labeling substance and MACS beads (magnetic beads).

Examples of cell surface markers include a cell surface marker (CD45) of leukocytes, a cell surface marker (CD3) of T cells, a cell surface marker (CD4) of helper T cells, a cell surface marker (CD8) of cytotoxicity T cells, a cell surface marker (CD39) of γδ T cells, and the like.

Examples of labeling substances include fluorescent substances, biotin, avidin, and the like.

Examples of fluorescent substances include allophycocyanin (APC), phycoerythrin (PE), fluorescein isothiocyanate (FITC), Alexa Fluor 488, Alexa Fluor 647, Alexa Fluor 700, PE-Texas Red, PE-Cy5, PE-Cy7, and the like.

In addition, in the present specification, the term "stem cells" mean immature cells which have self-renewal capability, and differentiation and growth capacity. Stem cells include subpopulations such as pluripotent stem cells, multipotent stem cells, unipotent stem cells, and the like depending on differentiation ability.

The term "pluripotent stem cells" mean cells that cannot become an individual pet se, but have an ability to differentiate into all tissues and cells that constitute a living body.

The term "multipotent stem cells" mean cells that have an ability to differentiate into multiple types of tissues and cells, but not all types.

The term "unipotent stem cells" mean cells that have an ability to differentiate into specific tissues or cells.

Examples of pluripotent stem cells include embryonic stem cells (ES cells), EG cells, iPS cells, and the like.

ES cells can be produced by culturing an inner cell mass on feeder cells or in a medium containing LIF. Methods for producing ES cells are described in, for example, WO96/22362, WO02/101057, U.S. Pat. Nos. 5,843,780, 6,200,806, 6,280,718, and the like.

EG cells can be produced by culturing primordial germ cells in a medium containing mSCF, LIF, and bPGF (Cell, 70: 841-847, 1992).

iPS cells can be produced by introducing reprogramming factors such as Oct3/4, Sox2, and KIf4 (and c-Myc or n-Myc if necessary) into somatic cells (such as fibroblasts and skin cells) (Cell, 126: p. 663-676, 2006; Nature, 448: p. 313-317, 2007; Nat Biotechnol, 26: p. 101-106, 2008; Cell 131: p. 861-872, 2007; Science, 318: p. 1917-1920, 2007; Cell Stem Ceils 1: p. 55-70, 2007; Nat Biotechnol, 25: p. 1177-1181, 2007; Nature, 448: p. 318-324, 2007; Cell Stem Cells 2: p. 10-12, 2008; Nature 451: p. 141-146, 2008; Science, 318; p. 1917-1920, 2007).

Stem cells established by culturing an early embryo produced by nuclear transfer of a nucleus of a somatic cell are also preferable as pluripotent stem cells (Nature, 385, 810 (1997); Science, 280, 1256 (1998); Nature Biotechnology, 17, 456 (1999); Nature, 394, 369 (1998); Nature Genetics, 22, 127 (1999); Proc. Nat 1. Acad. Sci. USA, 96, 14984 (1999)), Rideout III et al. (Nature Genetics, 24, 109 (2000)).

Examples of multipotent stem cells include mesenchymal stem cells (MSC) that can be differentiated into cells such as adipocytes, osteocytes, and chondrocytes; hematopoietic stem cells that can be differentiated into hematopoietic cells such as leukocytes, erythrocytes, and platelets: neural stem cells that can be differentiated into cells such as neurons, astrocytes, and oligodendrocytes; and somatic stem cells such as myeloid stem cells and germ stem cells.

Multi potent stem cells are preferably mesenchymal stem cells.

The term "mesenchymal stem cells" mean stem cells that can be differentiated into all of or some of osteoblasts, chondroblasts, and lipoblasts.

The multipotent stem cells can be isolated from a living body by known methods. For example, mesenchymal stem cells can be collected from bone marrow, adipose tissue, peripheral blood, the umbilical cord, umbilical cord blood, and the like of mammals by general known methods. For example, it is possible to isolate human 1.5 mesenchymal stem cells by culture and passaging of hematopoietic stem cells after bone marrow aspiration (Journal of Autoimmunity, 30 (2008) 163-171). Multipotent stem cells can also be obtained by culturing the above-described pluripotent stem cells under appropriate induction conditions.

Among them, animal cells are preferably derived from an umbilical cord or umbilical cord blood, and are more preferably mesenchymal stem/stromal cells derived from an umbilical cord or umbilical cord blood, or mononuclear cells derived from umbilical cord blood.

In the present specification, the "mesenchymal stem/stromal cells" include cells (that is, mesenchymal cells) that belong to a mesenchymal type (mesodermal tissues) which are differentiated cells, and the above-described mesenchymal stem cells.

In addition, in the present embodiment, the animal tissues may be any tissue containing the above-described animal cells. Examples thereof include bone marrow, adipose tissue, the umbilical cord, the placenta, and the like, but are not limited thereto.

Among them, animal tissues are preferably tissues derived from the umbilical cord, that is, umbilical cord tissues.

From the cryopreserved product of the present embodiment, it is possible to recover a favorable number of viable cells after thawing (refer to examples to be described later). For example, after an elapse of 2 weeks, it is possible to recover 80% or more, preferably 90% or more, more preferably 95% or more, and even more preferably 100% of the number of viable cells to be recovered from non-frozen animal cells or animal tissues.

In addition, from the cryopreserved product of the present embodiment, it is possible to recover 80% or more, preferably 90% or more, more preferably 95% or more, and even more preferably 100% of the number of viable cells to be recovered from non-frozen animal cells or animal tissues, after an elapse of 1 month, after an elapse of 3 months, after an elapse of 6 months, after an elapse of 1 year, after an elapse of 3 years, after an elapse of 5 years, or after an elapse of 10 years, or after an elapse of longer than years (semi permanently).

From the cryopreserved product of tire present embodiment, viable cells can be recovered using a recovery method to be described later. Tire recovered viable cells can be used for medical treatment or research, and the like.

<Cryopreservation Method of Animal Cells or Animal Tissues>

In one embodiment, the present invention provides a cryopreservation method of animal cells or animal tissues in which the above-described solution for cryopreservation of animal cells or animal tissues is used.

According to the cryopreservation method of the present embodiment, cells can be frozen while maintaining cell viability. In addition, since the solution for cryopreservation which does not contain natural components derived from animals is used, animal cells or animal tissues can be used for clinical purposes as they are after being thawed.

The cryopreservation method of the present embodiment will be described in detail below.

First, animal cells or animal tissues are immersed in the above-described solution for cryopreservation. It is preferable that time, which is taken after animal cells or animal tissues to be immersed are collected from an animal from which they are derived, become shorter, because the number of viable cells becomes large accordingly. For example, it is preferable to use animal cells or animal tissues within 48 hours after being collected from an origin animal from which they are derived, it is more preferable to use animal cells or animal tissues within 36 hours, and it is even more preferable to use animal cells or animal tissues within 24 horns. For example, when animal tissues are umbilical cord tissues, it is possible to obtain umbilical cord tissues from a placenta and an umbilical cord collected from a mother after childbirth by separating umbilical cord tissues from the placenta after umbilical cord blood collection.

An immersion temperature is not particularly limited, and is preferably OX to 15° C. and is more preferably 1° C. to 7° C. from the viewpoint of suppressing enzyme activity low and preventing bacterial infection.

Immersion time is not particularly limited, but a lower limit is preferably 1 hour or longer. Meanwhile, an upper limit is preferably 18 hours or shorter and is more preferably 6 hours or shorter from the viewpoint of reducing the influence on cell epigenetics.

An immersion pressure is not particularly limited, and may be, for example, normal pressure.

A container for putting in the solution for cryopreservation and animal cells or animal tissues during immersion is not particularly limited. For example, a case of performing immersion in cold-resistant containers and freezing each of the containers is preferable in terms of saving the trouble. A degree of cold resistance is not particularly limited as long as the container can withstand a temperature at which animal cells or animal tissues are stored, lire container is preferably made of a material that can withstand, for example, −80° C., and the container is preferably made of a material that can withstand, for example, −200° C.

Examples of cold-resistant containers include con tamers made of synthetic resin such as polyethylene, polypropylene, polystyrene, polyethylene terephthalate, polycarbonate, and fluorinated ethylene propylene. Examples of forms of the container include a bag, a tube, and the like.

The container is preferably a container that can be sealed after putting in the solution for cryopreservation and animal cells or animal tissues, and is preferably a container in which the inside is sterilized.

Next, the animal cells or animal tissues are frozen while in an immersed state in the solution for cryopreservation, A final freezing temperature is not particularly limited, but is preferably −80° C. or lower, is more preferably −150° C. or lower, and is even more preferably −196.5° C. or lower. A cooling rate is not particularly limited, but cooling at a slow rate is preferable. In a case of cooling at a slow rate, a BICELL and the like may be used, for example. For example, in a case where storage at around −80° C. is desired, it is preferable to perform cooling by taking time of 0.5 hours to 5 hours to reach that temperature. Alternatively, animal cells or animal tissues stored at around −80° C. may be transferred to be stored at −200° C. to −180° C. (for example, in liquid nitrogen or the like), it is preferable to put animal cells or animal tissues in a cold-resistant container to freeze them.

It is possible to recover a favorable number of viable cells of animal cells or animal tissues cryopreserved by using the cryopreservation method of the present embodiment after thawing (refer to tire examples to be described below). Recovery of viable cells can be performed according to, for example, a "[Method for recovering viable cells from cryopreserved animal cells or animal tissues]" to be described later.

From the animal cells or animal tissues cryopreserved by using the cryopreservation method of the present embodiment, it is possible to recover a favorable number of viable cells after thawing. For example, after a lapse of 2 weeks, it is possible to recover 80% or more, preferably 90% or more, more preferably 95% or more, and even more preferably 100% of the number of viable cells to be recovered from non-frozen animal cells or animal tissues.

In addition, from the animal cells or animal tissues cryopreserved by using the cryopreservation method of the present embodiment, it is possible to recover 80% or more, preferably 90% or more, more preferably 95% or more, and even more preferably 100% of the number of viable cells to be recovered from non-frozen animal cells or animal tissues, after a lapse of 1 month, after a lapse of 3 months, after a lapse of 6 months, after a lapse of 1 year, after a lapse of 3 years, after a lapse off years, or after a lapse of 10 years, or after a lapse of longer than 10 years (semi permanently).

Accordingly, when animal cells or animal tissues are cryopreserved by using the cryopreservation method of the present embodiment in advance, they can be thawed and used in future medical treatment of oneself and others. In addition, this cryopreservation can be effectively used when, in the future, it becomes possible to isolate unknown cells which may not have been sorted by the present technology. For example, when a treatment method is developed in the future for diseases for which there is no treatment method at present, it becomes possible to utilize annual cells or animal tissues cryopreserved in advance. Furthermore, in congenital genetic diseases and the like, this cryopreservation can also be utilized as a cell source of one's own for gene treatment.

[Method for Recovering Viable Cells from Cryopreserved Animal Cells or Animal Tissues]

In one embodiment, the present invention provides a method for recovering viable cells from cryopreserved animal cells or animal tissues, the method including a thawing step of thawing animal cells or animal tissues cryopreserved by using the above-described cryopreservation method.

According to the recovering method of the present embodiment, since the solution for cryopreservation which does not contain natural components derived from animals is used, animal cells or animal tissues can be used for clinical purposes as they are after being thawed.

A temperature in the thawing is not particularly limited, and is preferably 10° C. to 40° C. and is more preferably 30° C. to 40° C., Thawing is preferably performed rapidly, and thawing may be performed by using a water bath at, for example, 37° C. to 38° C. Thawing may be performed by taking out animal cells or animal tissues from a container in which the animal cells or animal tissues are stored in the above-described cryopreservation method, but it is preferable to thaw the container itself.

The recovery method of the present embodiment may include a washing step of removing the solution for cryopreservation attached to the thawed animal cells or animal tissues.

A liquid used in the washing step may be appropriately selected according to the contents of the subsequent treatment and the use purpose of cells. For example, washing may be performed by using the above-mentioned physiological solution or the like. The washing step is preferably performed immediately after the thawing step.

Next, in a case where a cryopreserved object is an animal tissue, the recovery method may include a cell recovery step of recovering viable cells from the thawed animal tissues, after the thawing step or the washing step.

A method for recovering cells is not particularly limited. For example, it is possible to use known methods for recovering cells from animal tissues. As one example, a method for performing cell culture by an explant method is exemplified.

In the cell culture by the explant method, animal tissues are shredded, tissue fragments are attached to a cell culture dish, and culture is performed for about 9 to 21 days. Thereafter, the cells are peeled off together with the tissue fragments with trypsin, the tissue fragments are removed by using a mesh (a cell strainer or the like may be used), and then only foe cells are recovered.

Accordingly, in one embodiment of the recovery method of the present embodiment, the method includes a culture step of performing cell culture by an explant method, before the cell recovery step.

In addition, there is a method in which tissue fragments shredded by using enzymes such as collagenases are separated to obtain cells. It is preferred to perform the washing step before the culture step.

Furthermore, as described above, in the cryopreservation method of the present embodiment, cells or tissues can be semi permanently preserved in a favorable state. Therefore, these cells or tissues can be used in a cell recovery method to be developed in the future.

Viable cells recovered by the recovery method of the present embodiment are not particularly limited, and examples thereof include the same as the animal cells exemplified in the above-described "<Cryopreserved products of animal cells or animal tissues>." In addition, viable cells may be unknown cells which cannot be separated at present.

Viable cells recovered are not limited to the original cells contained in animal tissues, and may be cells grown in the culture step (that is, copies of the original cells). The recovered viable cells can be used for medical treatment or research, and the like.

Using the cryopreservation method and the recovery method of the present embodiment, cells with a low degree of differentiation, such as stem cells or precursor cells, can be recovered in that state (refer to the examples to be described later).

Accordingly, in one embodiment, the present invention provides a differentiation method in which viable cells recovered by using the above-mentioned recovery method or cells obtained by subculturing the viable cells axe differentiated into desired cells. The subculture and a method of differentiation into desired cells may be performed according to known methods, for example.

<Kit for Cryopreservation of Animal Cells or Animal Tissues>

In one embodiment, the present invention provides a kit for cryopreservation of animal cells or animal tissues which includes the above-described solution for cryopreservation, and a cold-resistant container capable of storing the solution for cryopreservation and animal cells or animal tissues.

According to the kit for cryopreservation of the present embodiment, cells can be frozen while maintaining cell suability. In addition, since the solution for cryopreservation which does not contain natural components derived from animals is used, animal cells or animal tissues can be used for clinical purposes as they are after being thawed.

In addition, the kit for cryopreservation of the present embodiment is suitably used in the above-described "<Cryopreservation method of animal cells or animal tissues>."

The container is not particularly limited as long as it can store the solution for cryopreservation and animal cells or animal tissues and is cold resistant. A size of the container may be appropriately selected according to a size of animal cells or animal tissues to be stored. The container may be, for example, a box-shaped container having a side of 1 cm to 10 cm, or a bag having a side of 3 cm to 15 cm. In addition, tire container may be a freezing tube generally used in cryopreservation of cells and tissue fragments.

A degree of cold resistance is not particularly limited as long as the container can withstand a temperature at which animal cells or animal tissues are stored. The container is preferably made of a material that can withstand, for example, −80° C. and the container is preferably made of a material that can withstand, for example, −200° C. Specific examples of cold-resistant containers include containers made of synthetic resin such as polyethylene, polypropylene, polystyrene, polyethylene terephthalate, polycarbonate, and fluorinated ethylene propylene.

The kit for cryopreservation of the present embodiment may further include instructions for use of the kit. In the instructions for use of the kit, the contents of the cryopreservation method of the present embodiment described in the "<Cryopreservation method of animal cells or animal tissues>" described above are recorded. In addition, in the instructions for use of the kit, the contents of the recovery method of the present embodiment described in the "[Method for recovering viable cells from cryopreserved animal cells or animal tissues]" described above may further be recorded.

EXAMPLES

Hereinafter, the present invention will be described in detail based on examples, comparative examples, and the like, but the present invention is not limited to these examples and the like.

Example 1

(1) Preparation of Solution 1 for Cryopreservation

A sterilised solution 1 for cryopreservation which contains 45 v/v % of a glucose-added dextran 40 injection solution (manufactured by Otsuka Pharmaceutical Factory, Inc.) (which contains 4.5 w/v % of a dextran concentration and 2.25 w/v % of a glucose concentration), 45 w/v % of BICANATE (registered trademark) (manufactured by Otsuka Pharmaceutical Factory, Inc.), and 10 v/v % of DMSO was prepared. The solution 1 for cryopreservation does not contain natural components derived from animals.

(2) Freezing of Mesenchymal Stem/Stromal Cells Derived from Umbilical Cord

Next, 1.0×10⁶ cells/mL of mesenchymal stem/stromal cells derived from an umbilical cord and 1 mL of the solution 1 for cryopreservation prepared in (1) were put in a tube, and a cap was closed and seated. Next, the tube was put in a Mr. Frosty and frozen at −80° C. of freezer. The next day, the tube was moved to a nitrogen tank (−196° C.) and stored.

(3) Thawing of Mesenchymal Stem/Stromal Cells Derived from Umbilical Cord

Next, two weeks after the start of freezing, tire mesenchymal stem/stromal cells derived from an umbilical cord which were frozen in (2) were put in a water bath at 37° C. to 38° C. and thawed. After thawing, the cells were washed with serum-free medium (RM) (manufactured by ROHTO Pharmaceutical Co., Ltd.), and then centrifuged at 1,800 rpm for 10 minutes at 4° C. Next, the supernatant was removed, and 1 mL of serum-free medium (RM) (manufactured by ROHTO Pharmaceutical Co., Ltd.) was added to a pellet and suspended. Next, a total number of cells was measured by using an OneCell Counter under a stereo microscope (XN-100). In addition, when the total number of cells and the number of dead cells were measured by using a trypan blue staining method and a percentage of viable cells was calculated, the percentage was as high as 95.4%, which was the same percentage of viable cells as that of a case in which a solution for cryopreservation of the related art was used. Trypan blue cannot permeate cell) membranes of viable cells, and only permeates dead cells to stain them blue. As trypan blue, 0.4 to 0.5 w/v % of a commercially available product was used.

(4) Growth Test of Mesenchymal Stem/Stromal Cells Derived from Umbilical Cord after Freezing and Thawing Next, 1.0×10⁴ cells/well of the mesenchymal stem-stromal cells derived from an umbilical cord after freezing and thawing were seeded in a 6-well dish. The cells were recovered every 2 days, and the number of viable cells were measured to create a growth curve. The results are shown in FIG. 1.

Based on FIG. 1, it was confirmed that the mesenchymal stem/stromal cells derived from an umbilical cord after freezing and thawing proliferated without any problem. In addition, although not shown, a growth rate was at the same level as that of the case in which the solution for cryopreservation of the related art was used.

Example 2

(1) Preparation of Solution 1 for Cryopreservation to Solution 6 for Cryopreservation The solution 1 for cryopreservation to solution 6 for cryopreservation were prepared such that content percentages of dextran, glucose, BICANATE, DMSO, and human serum albumin became values shown in Table 1 below. The solution 6 for cryopreservation has the same composition as drat of a conventional TEMCELL HS injection solution (a drug formulation for intravenous injection which contains mesenchymal stem/stromal cells derived from human bone marrow).

TABLE 11

| Solution for cryopreservation | Content percentage of dextran (w/v %) | Content percentage of glucose (w/v %) | Content percentage of BICANATE (v/v %) | Content percentage of DMSO (v/v %) | Content percentage of human serum albumin (w/v %) |
|---|---|---|---|---|---|
| 1 | 4.50 | 2.25 | 45.00 | 10.00 | 0.00 |
| 2 | 6.00 | 3.00 | 30.00 | 10.00 | 0.00 |
| 3 | 3.00 | 1.50 | 60.00 | 10.00 | 0.00 |
| 4 | 1.00 | 0.50 | 80.00 | 10.00 | 0.00 |
| 5 | 0.00 | 0.00 | 90.00 | 10.00 | 0.00 |
| 6 | 0.00 | 0.00 | 64.50 | 10.00 | 5.00 |

(2) Freezing of Mesenchymal Stem/Stromal Cells Derived from Umbilical Cord

Next, 1.0×10⁶ cells/mL of mesenchymal stem/stromal cells derived from an umbilical cord and 1 mL of the solution 1 for cryopreservation prepared in (1) were put in a tube, and a cap was closed and sealed. Next, the tube was put in a Mr. Frosty and frozen, at −80° C. of freezer. The next day, the tube was moved to a nitrogen tank (−196° C.) and stored.

(3) Thawing of Mesenchymal Stem/Stromal Cells Derived from Umbilical Cord

Next, two weeks after the start of freezing, the mesenchymal stem/stromal cells derived from an umbilical cord which were frozen in (2) were put in a water hath at 37° C. to 38° C. and thawed After thawing, the cells were washed with serum-free medium (RM) (manufactured by ROHTO Pharmaceutical Co., Ltd.), and then centrifuged at 1,200 rpm for 5 minutes at 4° C. Next, the supernatant was removed, and 1 mL of serum-free medium (RM) (manufactured by ROHTO Pharmaceutical Co., Ltd.) was added to a pellet and suspended. Next, a total number of cells and the number of dead cells were measured using a Countess by a trypan blue method, lire number of viable cells per mL, and a percentage of viable cells calculated from the total number of cells and the number of dead cells are shown in Table 2 below. In addition, a recovery percentage was calculated from the number of viable cells after freezing with respect to the number of viable cells ($1\times10^6$/mL) before freezing, and is shown in Table 2 below.

TABLE 2

| Solution for cryopreservation | Percentage of viable cells (%) | Number of viable cells after freezing and thawing ($\times10^5$/mL) | Recovery percentage (%) |
|---|---|---|---|
| 1 | 98.90 | 9.40 | 94.00 |
| 2 | 98.70 | 7.80 | 78.00 |
| 3 | 95.30 | 8.15 | 81.50 |
| 4 | 94.70 | 8.05 | 80.50 |
| 5 | 93.30 | 7.60 | 76.00 |
| 6 | 99.50 | 9.85 | 98.50 |

(4) Growth Test of Mesenchymal Stem/Stromal Cells Derived from Umbilical Cord after Freezing and Thawing Next, $1.0\times10^4$ cells/well of the mesenchymal stem/stromal cells derived from, an umbilical cord after freezing and thawing were seeded in a 24-well plate. The cells were recovered every 2 days, and the number of viable cells were measured to create a growth curve. The results are shown in FIG. 2.

Based on Table 2, in all cells obtained by using any of the solutions for cryopreservation, percentages of viable cells were 90% or more, and thus were favorable. Meanwhile, the solution 1 for cryopreservation in which a dextran concentration was 4.5 w/v % showed the most favorable recovery percentage that was at the same level as that of the solution 6 for cryopreservation which has the same composition as that of the TEMCELL HS injection solution. In addition, in a case where a concentration of dextran was 0 or high, a recovery percentage of viable cells was poor.

Figure 2:
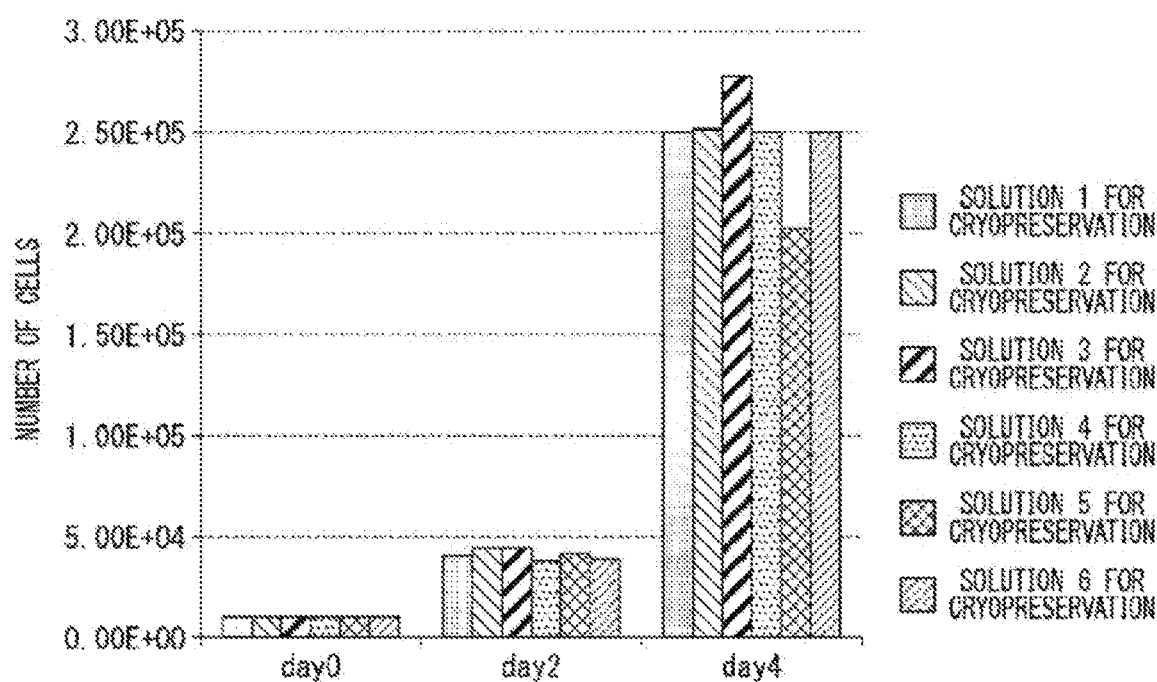
FIG. 2 is a graph showing the numbers of cells after 0, 2, and 4 days from culture performed after thawing umbilical cord-derived cells, which had been frozen by using solution 1 to solution 6 for cryopreservation in Example 2.

Furthermore, based on FIG. 2, a growth rate of the solution 1 for cryopreservation to the solution 4 for cryopreservation which contain dextran was at the same level as that of the solution 6 for cryopreservation which has the same composition as that of the TEMCELL HS injection solution. Meanwhile, in the case of the solution for cryopreservation in which a concentration of dextran was 0, a reduction in growth rate was observed despite the same number of viable cells being seeded.

Example 3

(1) Preparation of Solution 1 for Cryopreservation and Solution 7 for Cryopreservation to Solution 11 for Cryopreservation The solution 1 for cryopreservation and solution 7 for cryopreservation to solution 11 for cryopreservation were prepared such that content percentages of dextran, glucose, BICANATE, DMSO, and a citric acid hydrate and a sodium citrate hydrate derived from the solution A in the biological products standard blood preservation solutions (an ACD-A solution) (manufactured by Terumo Corporation) became values shown in Table 3 below. As the ACD-A solution, a solution containing 2.20 w/v % of sodium citrate hydrate, 0.80 w/v % of citric acid hydrate, and 2.20 w/v % of glucose was used.

TABLE 3

| Solution for cryopreservation | Content percentage of dextran (w/v %) | Content percentage of glucose (w/v %) | Content percentage of BICANATE (v/v %) | Content percentage of DMSO (v/v %) | Content percentage of citric acid hydrate and Na citrate hydrate (w/v%) |
|---|---|---|---|---|---|
| 1 | 4.50 | 2.25 | 45.00 | 10.00 | 0.00 |
| 7 | 0.00 | 0.00 | 100.00 | 0.00 | 0.00 |
| 8 | 4.50 | 2.25 | 55.00 | 0.00 | 0.00 |
| 9 | 4.50 | 2.75 | 42.75 | 10.00 | 0.68 |
| 10 | 0.00 | 0.50 | 97.75 | 0.00 | 0.68 |
| 11 | 4.50 | 2.75 | 52.75 | 0.00 | 0.68 |

(2) Measurement of pH of Solution 1 for Cryopreservation and Solution 7 for Cryopreservation to Solution 11 for Cryopreservation Next, a pH of each of the solution 1 for cryopreservation and solution 7 for cryopreservation to solution 11 for cryopreservation was measured after 0 minutes, 30 minutes, 1 hour, 2 hours, 3 hours, 4 hours, 5 hours, and 6 hours from tire preparation. Changes over time in the pH of each of the solutions for cryopreservation are shown in FIG. 3.

Figure 3:
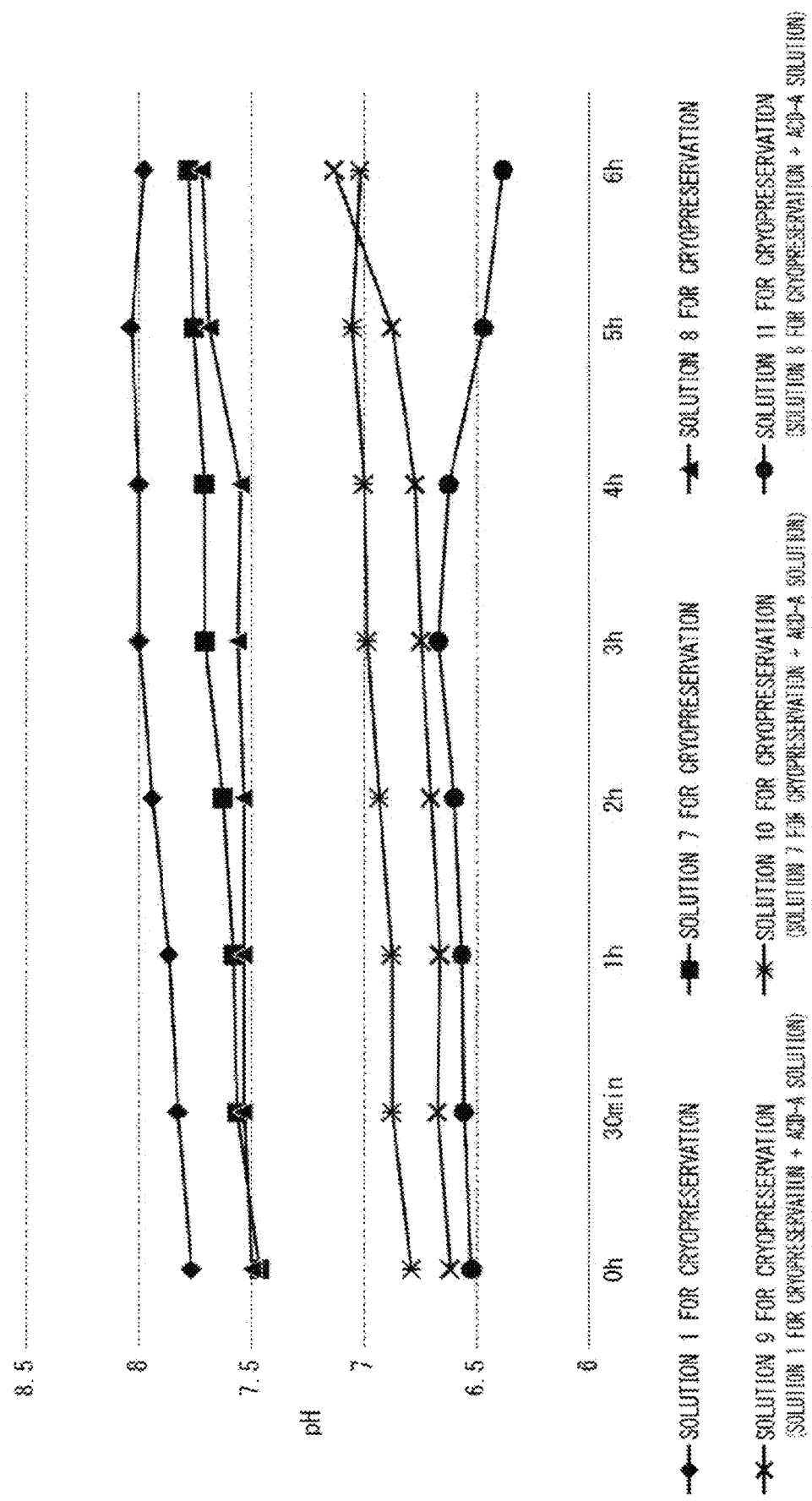
FIG. 3 is a graph showing change in pH after 0 minutes, 30 minutes, 1 hour, 2 hours, 3 hours, 4 hours, 5 hours, and 6 hours from preparation of a solution 1 for cryopreservation and a solution 7 for cryopreservation to a solution 11 for cryopreservation in Example 3.

Based on FIG. 3, in the solutions for cryopreservation to which tire ACD-A solution was added, a pH was 7.5 or less and was stable over time.

(3) Freezing and Thawing of Mesenchymal Stem/Stromal Cells Derived from Umbilical Cord Next, using the same method as that of (2) and (3) of Example 1 above and using the solution 9 for cryopreservation of Table 3 above, mesenchymal stem/stromal cells derived from three different donors were cryopreserved, and the cells were thawed after two weeks. Next, a total number of cells and the number of dead cells were measured using a Countess by a trypan blue staining method. A percentage of viable cells calculated from the measured total number of cells and the measured number of dead cells averaged 90% (92%, 87%, and 90%), and thus was favorable.

In addition, changes in viability in a case of storage under refrigeration after thawing are shown in Table 4 below.

TABLE 4

| | Elapsed time (time) | | | | | | |
|---|---|---|---|---|---|---|---|
| | 0.0 | 0.5 | 1.0 | 1.5 | 2.0 | 2.5 | 3.0 |
| Percentage of viable cells (%) | 94 | 90 | 92 | 92 | 93 | 90 | 96 |

Based on Table 4, it was confirmed that a percentage of viable cells could be maintained at 90% or more for indicated time after thawing.

Example 4

(1) Preparation of Solution 1 for Cryopreservation, Solution 2 Tor Cryopreservation, and Solution 5 for Cryopreservation The solution 1 for cryopreservation, solution 2 for cryopreservation, and solution 5 for cryopreservation were prepared such that content percentages of dextran, glucose, BICANATE, and DMSO became values shown in Table 1 above.

(2) Freezing of Mononuclear Cells Derived from Umbilical Cord Blood

Next, umbilical cord blood-derived mononuclear cells (MNC) were separated from a human umbilical cord blood sample by using a Ficoll density gradient centrifugation method. Next, $1.0 \times 10^7$ cells/mL of MNCs derived from umbilical cord blood and 1 ml, of each of the solution 1 for cryopreservation, the solution 2 for cryopreservation, and the solution 5 for cryopreservation which were prepared in (1) were put in a tube, and a cap was closed and sealed. Next, the tube was put in a Mr. Frosty and frozen at −80° C. of freezer. The next day, the tube was moved to a nitrogen tank (−196° C.) and cryopreserved for about one month from the start of freezing.

(3) Thawing of Mononuclear Cells Derived from Umbilical Cord Blood

Next, about one month after the start of freezing, the mononuclear cells derived from umbilical cord blood which were frozen in (2) were put in a water bath at 37° C. to 38'T and thawed. After thawing, the cells were washed with RMPI 1640 medium (containing 10% fetal bovine serum), and then centrifuged at 1,800 rpm for 10 minutes at 4° C. Next, the supernatant was removed, and 1 ml, of RMPI 1640 medium (containing 10% fetal bovine serum) was added to a pellet and suspended Next, a total number of cells was measured by using an automatic multi-parameter hematology analyzer Sysmex (XN-1000). In addition, a total number of cells and the number of dead cells were measured by using an AO/EB method. AO indicates acridine orange, and stains both viable cells and dead cells. In addition, EB indicates ethidium bromide, which cannot permeate cell membranes of viable cells and only permeates dead cells to stain them. Accordingly, viable cells are stained green, and dead cells are stained orange.

The number of viable cells per mL, and a percentage of viable cells calculated from the total number of cells and the number of dead cells are shown in Table 5 below. In addition, a recovery percentage was calculated from the number of viable cells after freezing with respect to the number of viable cells ($1 \times 10^7$/mL) before freezing, and is shown in Table 5 below.

TABLE 5

| Solution for cryopreservation | Percentage of viable cells (%) | Number of viable cells after freezing and thawing ($\times 10^6$/mL) | Recovery percentage (%) |
|---|---|---|---|
| 1 | 91.60 | 8.90 | 89.0 |
| 2 | 93.30 | 8.80 | 88.0 |
| 5 | 90.70 | 8.20 | 82.0 |

Based on Table 5, in the solution for cryopreservation which contains dextran, a percentage of viable cells was 90% or more, a recovery percentage was 85% or more, and thus both were favorable. On the other hand, in the ease of the solution for cryopreservation which does not contain dextran, a percentage of viable cells was 90% or more, but a recovery percentage was 82%, which is less than 85%.

Based on the above descriptions, it was confirmed that using of the solutions for cryopreservation which contain a specific concentration of dextran enabled freezing of cells while maintaining cell viability and a favorable growth rate after thawing of cells.

Example 5

(1) Preparation of Solution 12 for Cryopreservation

The solution 12 for cryopreservation was prepared such that content percentages of dextran, BICANATE, DMSO, and a citric acid hydrate, sodium citrate hydrate, and glucose derived from the solution A in the biological products standard blood preservation solutions (an ACD-A solution) (manufactured by Terumo Corporation) became values shown in Table 6 below. As the ACD-A solution, a solution containing 2.20 w/v % of sodium citrate hydrate, 0.80 w/v % of citric acid hydrate, and 2.20 w/v % of glucose was used.

TABLE 6

| Solution for cryopreservation | Content percentage of dextran (w/v %) | Content percentage of glucose (w/v %) | Content percentage of BICANATE (v/v %) | Content percentage of DMSO (v/v %) | Content percentage of citric acid hydrate and Na citrate hydrate (w/v%) |
|---|---|---|---|---|---|
| 12 | 4.50 | 0.02475 | 43.875 | 10.00 | 0.03375 |

(2) Freezing of Mesenchymal Stem/Stromal Cells Derived from Umbilical Cord

Next, a frozen umbilical cord was thawed to recover mesenchymal stem/stromal cells (MSC) by using an explant method. Next, the recovered MSCs were cultured, and cells were recovered when reached 70 to 80% confluence. Next, tire recovered cells were frozen again and then thawed. The thawed cells were cultured. The passages were repeated, and cells were cultured from P4 to P5. Next, the subcultured MSCs and the solution 12 for cryopreservation prepared in (1) were put in a tube, and a cap was closed and sealed. Next, the tube was put in a Mr. Frosty and frozen in a freezer at −80° C. The next day, the tube was moved to and stored in a nitrogen tank (−196° C.) to be cryopreserved for about one month from the start of freezing.

(3) Thawing of MSCs Derived from Umbilical Cord

Next, about one month after the start of freezing, the MSCs derived from an umbilical cord which were frozen in (2) were put in a water bath at 37° C. to 38° C. and thawed. After thawing, the cells were washed with serum-free medium (RM) (manufactured by ROHTO Pharmaceutical Co., Ltd.), and then centrifuged at 1,800 rpm for 10 minutes at 4° C. Next, the supernatant was removed, and 1 ml of RM was added to a pellet and suspended, (4) Detection of Cell Surface Marker Next, cell surface markers were detected by flow cytometry using antibodies against various cell surface markers. Cell surface markers to be detected are CD73, CD105, CD90, CD44, HLA-ABC, CD45, HLA-DR, CD34, CD11b, and CD19. The results are shown in FIG. 4.

Figure 4:
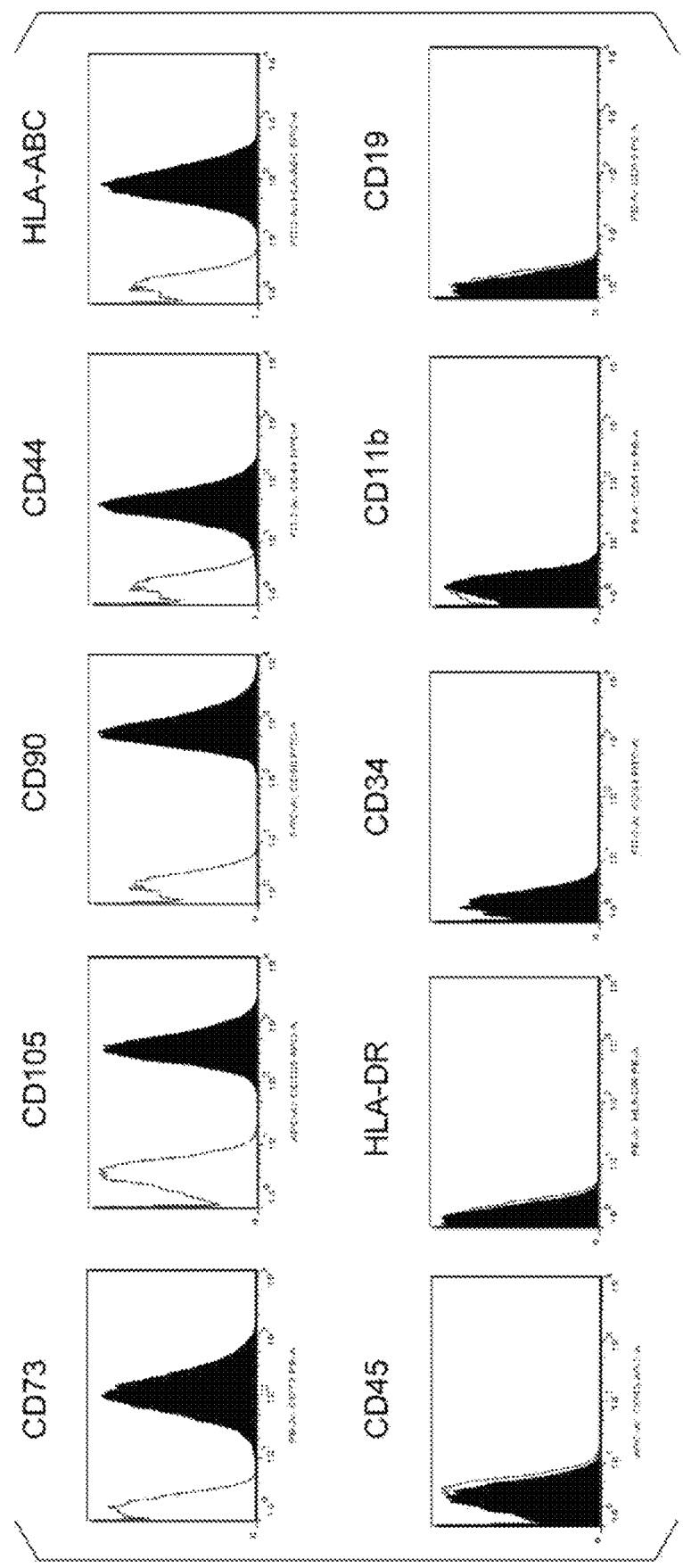
FIG. 4 shows graphs showing results of detection of various cell surface markers of umbilical cord-derived Mesenchymal stem/stromal cells (MSC), which had been frozen by using a solution 12 for cryopreservation in Example 5 and thawed.

Based on FIG. 4, various cell surface markers were detected in MSCs that were frozen and thawed by using the solution 12 for cryopreservation. Specifically, the cells subjected to freezing and thawing were CD73, CD105, CD90, CD44, and MLA-ABC positive; and were CD45, HLA-DR, CD34, CD11b, and CD19 negative. Accordingly, cell properties after freezing and thawing matched those before freezing, and foe cells after freezing and thawing fitted foe definition of MSC.

(5) Continuation of Differentiation Capacity of MSC

Next, differentiation of the cells thawed in (3) into adipocytes, osteoblasts, and chondroblasts was induced by using a known method. Specifically, the differentiation was performed by the following procedure.

(5-1) Differentiation-Induced into Adipocyte and Oil Red O Staining

•Differentiation Induction into Adipocytes

A cell suspension of $5\times10^4$ cells/mL of MSCs was prepared, was added to a 12-well plate by 1 ml/well, and cultured in advance. In addition, 10 mL of differentiation induction culture media having a composition shown in Table 7 below were prepared in advance. Next, when the cells reached 80% confluence, the medium was changed to a differentiation induction medium having the composition shown in Table 7 below, and cells were cultured for 3 to 4 weeks to be differentiation-induced into adipocytes. The medium was changed every three days.

TABLE 7

| Composition | Final concentration | Amount | Manufacturer name/model No. |
|---|---|---|---|
| αMEM (containing 10% FBS and antibiotic substance) | — | 10 μL | Wako 135-15175 |
| Indomethacin | 100 μM | 18 μL | Wako 093-02473 |
| Dexamethasone | 1 μM | 100 μL | Wako 047-18863 |
| IBMX | 0.5 μM | 5 μL | Sigma 15789-100MG |
| Insulin | 10 μM/mL | 10 μL | Sigma |

•Oil Red O Staining

When lipid droplet-like cysts in the cells were checked with a microscope during culture, the medium was sucked to be removed. Next, the cells were washed twice with 1 mL of PBS. Next, 1 mL of 10% formalin was added, and the mixture was allowed to stand for 10 minutes. Next, the cells were washed twice with 1 mL of PBS. Next, 1 mL of 60% isopropanol was added, the mixture was allowed to stand for 1 minute, and then isopropanol was removed. Next, 1 mL of a staining solution was added.

The staining solution was prepared by the following procedure. First, 10 mL of 99% isopropanol was added to 30 mg of oil red O and mixed to prepare an oil red O solution. Next, 6 mL of the oil red O solution and 4 mL of ultrapure water were mixed and further mixed by shaking with a vortex. Next, the mixture was passed through a 2.2 mL filter, and therefore the staining solution was obtained. The staining solution was shielded from light by aluminum foil until use.

Figure 5:
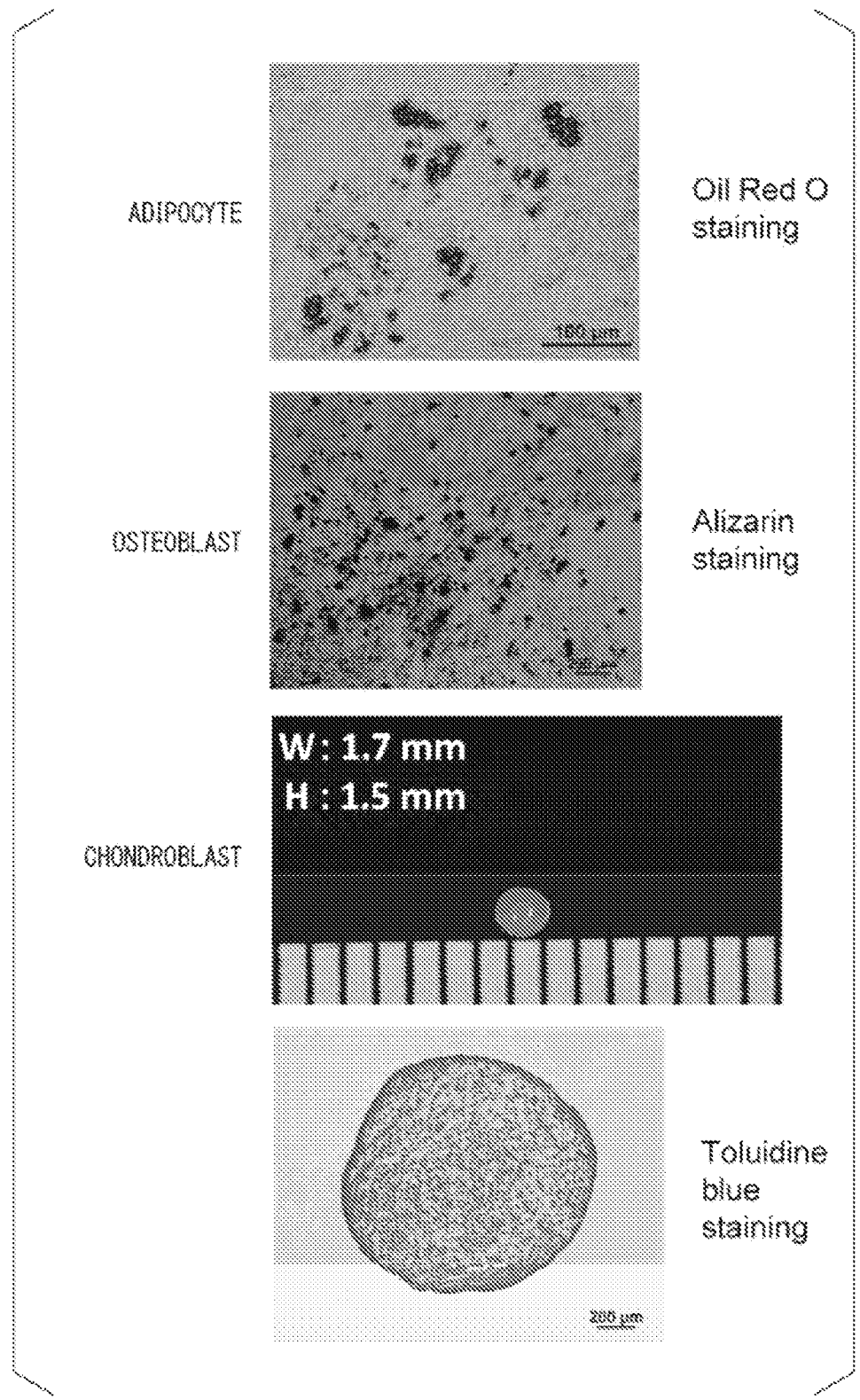
FIG. 5 shows microscopic images of adipocytes, osteoblasts, and chondroblasts, which were differentiation-induced from umbilical cord-derived MSCs, which had been frozen by using the solution 12 for cryopreservation in Example 5 and thawed. A scale bar for the adipocytes is 100 μm. A scale bar for the osteoblasts is 200 μm. A scale bar for the chondroblasts is 200 μm.

Next, a plate to which the staining solution was added was allowed to stand for 20 to 30 minutes while being shielded from light by aluminum foil. Next, the plate was washed with 1 mL of 60% isopropanol and then washed twice with 1 mL of PBS. Next, observation was performed using a microscope. The results are shown in FIG. 5. In the adipocytes of FIG. 5, it was checked that lipid droplets were stained red. In FIG. 5, a scale bar for the adipocytes is 100 μm.

(5-2) Differentiation Induction into Osteoblasts and Alizarin Staining

•Differentiation Induction into Osteoblasts

A bone differentiation-induced medium (manufactured by Gibco, "StemPro (registered trademark) Osteocyte/Chondrocyte" (product name), model number: A10072-01) was thawed in advance, and an antibiotic substance (manufactured by Gibco, model number: 15240-062) was added thereto such that a final concentration became 1 v/v %. The mixture was dispensed by 10 mL and frozen until required. A cell suspension of $3\times10^4$ cells/mL of MSCs was prepared, was added to a 12-well plate by 1 ml/well, and cultured. Next, when the cells reached 80% confluence, the medium was changed to the differentiation-induced medium which was dispensed and frozen. Cells were cultured for 9 days to be differentiation-induced into osteoblasts.

•Alizarin Staining

After black calcium precipitates were checked on the cultured cells with a microscope, the medium was sucked to be removed, and the cells were washed with PBS. Next, a fixing solution (at room temperature) was added, and the mixture was fixed for seconds.

The fixing solution was prepared by the following procedure. First, 1.5 M trisodium citrate dihydrate was added to 1.5 M citric acid monohydrate, and a pH was adjusted to 3.0 Therefore, a 1.5 M citric acid buffer solution (pH 3.0) was produced and stored at 4° C. Next, 20 mL of ultrapure water was added to 400 μL of the 1.5 M citric acid buffer solution (pH 3.0) to dilute the solution, and therefore a standard citric acid-diluted solution was prepared Next, 12 mL of the standard citric acid-diluted solution, (at room temperature) was added to 18 mL of acetone m obtain the fixing solution.

Next, the fixing solution was removed. Next, ultrapure water was added. After the mixture was allowed to stand for 45 seconds, the ultrapure water was removed, and the cells was washed. Next, 1 mL of a staining solution was added, and the mixture was allowed to stand for 30 minutes at room temperature under light-shielded conditions to stain the cells.

The staining solution was prepared by the following procedure. First, 9.6 mL of ultrapure water was added to and mixed with 3 to 5 mg of FAST BLUE RR SALT (manufactured by Sigma-Aldrich). 0.4 mL of Naphthol AS-MX Phosphate Alkaline Solution (manufactured by Sigma-Aldrich) was added thereto to obtain the staining solution. The staining solution was shielded from tight, by aluminum foil until use.

Next, the staining solution was removed. Next, ultrapure water was added. After the mixture was allowed to stand for 2 minutes, the ultrapure water was removed, and the cells was washed. Next, ultrapure water was added again, and observation was performed using a microscope. The results are shown in FIG. 5. In the osteoblasts of FIG. 5, it was observed that calcium deposits were stained red. In FIG. 5, a scale bar for the osteoblasts is 200 μm.

(5-3) Differentiation Induction into Chondroblasts and Toluidine Blue Staining

•Differentiation Induction into Chondroblasts

An antibiotic substance (manufactured by Gibco, model number: 15240-062) was added in advance to a chondrocyte differentiation-induced medium (manufactured by Miltenyi Biotec, "NH ChondroDiff Medium" (product name), model number: 130-091-679) such that a final concentration became 1 v/v %. Next, using the chondrocyte differentiation-induced medium, a cell suspension of $2.5 \times 10^5$ cells/mL of MSCs was prepared. Next, 1 mL of the cell suspension was transferred to a 15 ml, conical tube (made of polypropylene). Next, the tube was centrifuged at 150×g for 5 minutes at room temperature. Next, the supernatant was removed, and 1 mL of the chondrocyte differentiation-induced medium was added thereto as not to destroy a pellet. The mixture was again centrifuged at 150 g for 5 minutes at room temperature, the supernatant was removed, and 1 mL of the chondrocyte differentiation-induced medium was added. Next, the cells were cultured in a CO: incubator for 24 days to be differentiation-induced into chondroblasts. The medium was changed every three days. After 24 days, a size of a chondroblast mass was confirmed to be 1.7 mm in width and 1.5 mm in height (refer to FIG. 5).

•Toluidine Blue Staining

Next, by a known method, a thin section of the chondroblast mass was produced and fixed to a prepared slide, and subjected to toluidine blue staining. Metachromatic stain was observed with a microscope. The results are shown in FIG. 5. In FIG. 5, a scale bar for the chondroblasts is 200 μm.

Based on FIG. 5, it was confirmed MSCs were differentiation-induced into adipocytes, osteoblasts, and chondroblasts. Accordingly, it was confirmed that differentiation capacity was maintained in tire MSCs that were frozen and thawed by using the solution 12 for cryopreservation.

(6) Confirmation of In Vitro Immunosuppressive Ability of MSC

Next, the cells thawed in (3), CFSE-stained mononuclear cells as a Responder, and dendritic cells as a Stimulator were co-cultured (hereinafter referred to as "R+S+MSC (DBA-D)"). In addition, the cells thawed in (3) and the CFSE-stained mononuclear cells were co-cultured using a medium containing phytohemagglutinin-L (PHA-L) (hereinafter referred to as "R+PHA-L+MSC (DBA-D)").

Furthermore, cells obtained by culturing only the CFSE-stained mononuclear cells (hereinafter referred to as "R") were prepared as a control group 1, Cells obtained by co-culturing the CFSE-stained mononuclear cells and the dendritic cells (hereinafter referred to as "R+S") were prepared as a control group 2. Cells obtained by culturing the CFSE-stained mononuclear cells using a medium containing PHA-L (hereinafter referred to as "R+PHA-L") were prepared as a control group 3.

Figure 6:
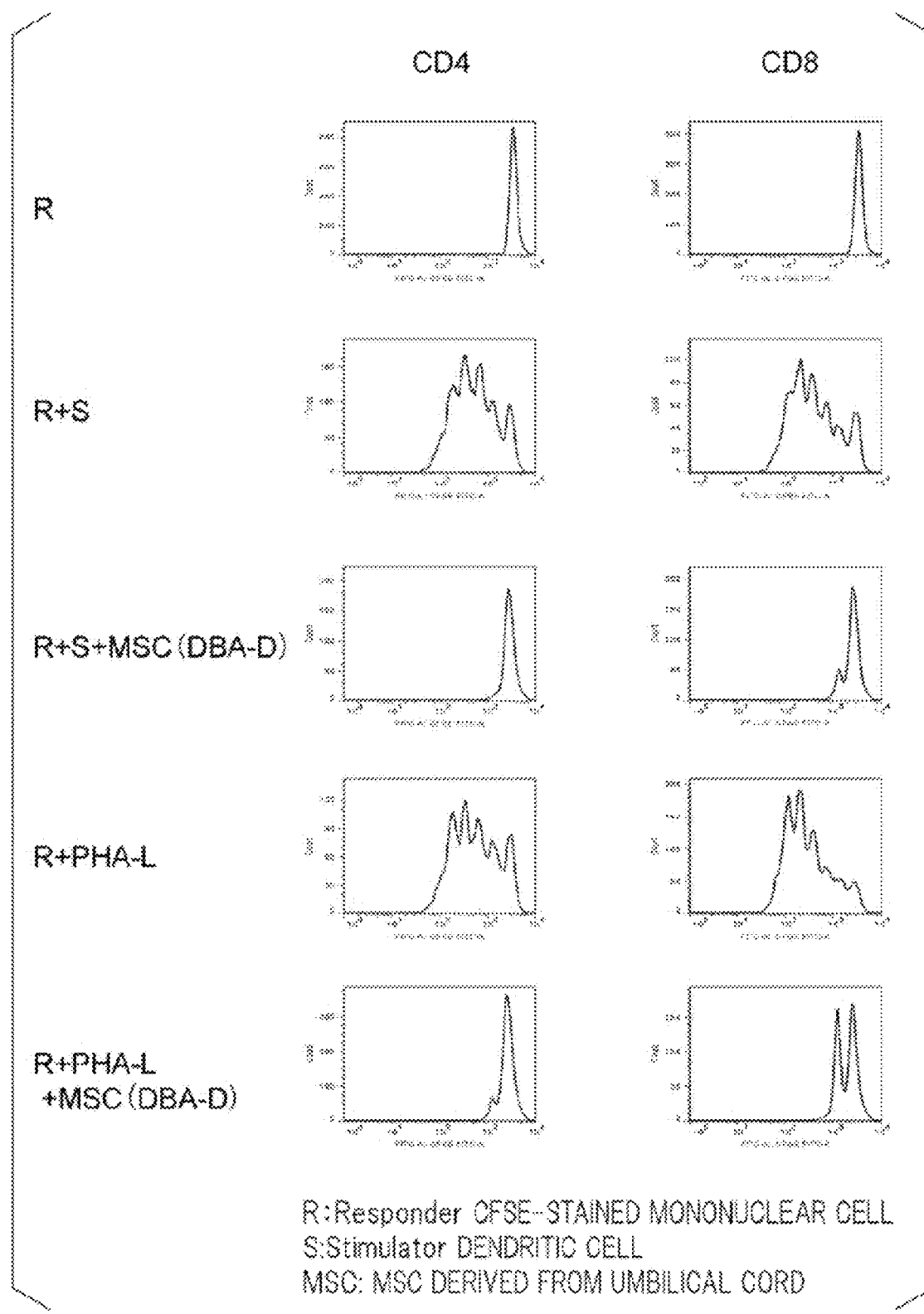
FIG. 6 shows graphs showing results of a confirmation test on the immunosuppressive ability of umbilical cord-derived MSCs, which had been frozen by using the solution 12 for cryopreservation in Example 5 and thawed.

Each of cultured cells was stained by using an antibody against CD4 and CD8 as a cell surface marker, and then CD4 and CD8 were detected by flow cytometry. The results are shown in FIG. 6. In FIG. 6, tire "R" indicates CFSE-stained mononuclear cells as a Responder. The "S" indicates dendritic cells as a Stimulator. The "MSC (DBA-D)" indicates MSCs derived from an umbilical cord which have been frozen and thawed by using the solution 12 for cryopreservation. The "PHA-L" indicates phytohemagglutinin-L (PHA-L).

In FIG. 6, in the case of only the Responders (the control group 1, which is the "R"), cells do not grow and divide, and $CD4^+$ cells and $CD8^+$ cells of the CFSE-stained Responder have one peak. However, because the $CD4^+$ cells and CDR cells of the Responder were activated and grew when they were mixed with the "S," fluorescent brightness of CFSE was halved according to the cell division, and a peak was shifted gradually to the left (the control group 2, which is "R+S"). In addition, when the $CD4^+$ cells and $CD8^+$ cells of the Responder were co-cultured with the cells (MSC) thawed in (3) ("R+S+MSC (DBA-D)"), a peak stops at the same position as that of the control group 1 (the "R"), and it was checked that growth of the $CD4^+$ cells and $CD8^+$ cells of the Responder was suppressed. Similarly, the $CD4^+$ cells and $CD8^+$ cells of the Responder were activated and grew when PHA-L was added thereto, a peak was shifted gradually to the left (the control group 3, which is "R+PHA-L"). In addition, when the $CD4^+$ cells and $CD8^+$ cells of the Responder were co-cultured with the cells (MSC) thawed in (3) ("R+PHA-L+MSC (DBA-D)"), a peak stops at the same position as that of the control group (the "R"), and it was checked that growth of the $CD4^+$ cells and $CD8^+$ cells of the Responder was suppressed.

Based on the above descriptions, immunosuppressive ability of the MSCs frozen and thawed by using the solution 12 for cryopreservation was confirmed.

INDUSTRIAL APPLICABILITY

According to the solution for cryopreservation of animal cells or animal tissues of the present embodiment, cells can be frozen while maintaining cell viability. In addition, animal cells or animal tissues, particularly human cells or human tissues, which are stored by using tire solution for cryopreservation of the present embodiment, are not made to contain natural protein components derived from animals, and thickeners such as sodium carboxymethylcellulose or polyethylene glycol. Therefore, the solution for cryopreservation is very useful in clinical use.

What is claimed is:

1. A cryopreserved product of mesenchymal cells or mesenchymal stem cells, comprising:
    mesenchymal cells or mesenchymal stem cells; and
    a solution for cryopreservation of mesenchymal cells or mesenchymal stem cells which substantially comprises a cryoprotectant that contains 3.0 w/v % to 4.5 w/v % of dextran or derivatives thereof or salts thereof, and dimethyl sulfoxide, and a physiological aqueous solution, and does not comprise serum.

2. The cryopreserved product of mesenchymal cells or mesenchymal stem cells according to claim 1, wherein the mesenchymal cells or mesenchymal stem cells are derived from an umbilical cord or umbilical cord blood.

3. A cryopreservation method of mesenchymal cells or mesenchymal stem cells, comprising:
    immersing mesenchymal cells or mesenchymal stem cells in a solution for cryopreservation of mesenchymal cells or mesenchymal stem cells; and freezing the mesenchymal cells or mesenchymal stem cells while in an immersed state in the solution for cryopreservation, wherein the solution substantially comprises a cryoprotectant that contains 3.0 w/v % to 4.5 w/v % of dextran or derivatives thereof or salts thereof, and dimethyl sulfoxide, and a physiological aqueous solution, and does not comprise serum.

4. The cryopreserved product of mesenchymal cells or mesenchymal stem cells according to claim 1, wherein the amount of dimethyl sulfoxide is 1.0 v/v % to 15.0 v/v %.

5. The cryopreserved product of mesenchymal cells or mesenchymal stem cells according to claim 1, wherein the solution further comprises citric acid or hydrates thereof or salts thereof, and a pH of the solution is 6.0 to 8.0.

6. The cryopreserved product of mesenchymal cells or mesenchymal stem cells according to claim 1, wherein the solution further comprises glucose.

7. The cryopreserved product of mesenchymal cells or mesenchymal stem cells according to claim 1, wherein the physiological aqueous solution comprises magnesium, potassium, calcium, sodium, and bicarbonate ions.

\* \* \* \* \*